(12) United States Patent
Ewers et al.

(10) Patent No.: US 7,942,898 B2
(45) Date of Patent: May 17, 2011

(54) DELIVERY SYSTEMS AND METHODS FOR GASTRIC REDUCTION

(75) Inventors: Richard C Ewers, Fullerton, CA (US); Vahid Saadat, Saratoga, CA (US); Eugene Chen, Carlsbad, CA (US)

(73) Assignee: USGI Medical, Inc., San Clemente, CA (US)

( * ) Notice: Subject to any disclaimer, the term of this patent is extended or adjusted under 35 U.S.C. 154(b) by 657 days.

(21) Appl. No.: 10/612,109

(22) Filed: Jul. 1, 2003

(65) Prior Publication Data

US 2004/0122473 A1    Jun. 24, 2004

Related U.S. Application Data

(60) Provisional application No. 60/433,065, filed on Dec. 11, 2002.

(51) Int. Cl.
  *A61B 17/04* (2006.01)
  *A61B 17/06* (2006.01)
(52) U.S. Cl. .......................... 606/222; 606/223; 606/232
(58) Field of Classification Search .................. 606/222, 606/232; 604/540, 541, 544
  See application file for complete search history.

(56) References Cited

U.S. PATENT DOCUMENTS

| | | |
|---|---|---|
| 616,672 A | 12/1898 | Kelling |
| 2,201,610 A | 5/1940 | Dawson, Jr. |
| 2,413,142 A | 12/1945 | Jones et al. |
| 2,510,198 A | 6/1950 | Tesmer |
| 2,533,494 A | 12/1950 | Mitchell, Jr. |
| 3,060,972 A | 10/1962 | Sheldon |
| 3,096,962 A | 7/1963 | Johannes |
| 3,150,379 A | 9/1964 | Brown |
| 3,162,214 A | 12/1964 | Bazinet, Jr. |
| 3,166,072 A | 1/1965 | Sullivan, Jr. |
| 3,168,274 A | 2/1965 | Street |
| 3,190,286 A | 6/1965 | Stokes |
| 3,430,662 A | 3/1969 | Guamaschelli |
| 3,494,006 A | 2/1970 | Brumlik |
| 3,546,961 A | 12/1970 | Marton |
| 3,551,987 A | 1/1971 | Wilkinson |
| 3,643,653 A | 2/1972 | Takahashi et al. |
| 3,646,615 A | 3/1972 | Ness |
| 3,664,345 A | 5/1972 | Dabbs et al. |
| 3,753,438 A | 8/1973 | Wood et al. |
| 3,858,578 A | 1/1975 | Milo |
| 3,867,944 A | 2/1975 | Samuels |

(Continued)

FOREIGN PATENT DOCUMENTS

EP    0 480 428 A2    4/1992

(Continued)

OTHER PUBLICATIONS

Angiolink, The Expanding Vascular Staple [brochure], 1 page total.

(Continued)

*Primary Examiner* — Melanie J Hand
(74) *Attorney, Agent, or Firm* — Charles C. Fowler; Levine Bagade Han LLP

(57) ABSTRACT

A delivery catheter for a gastric reduction system includes an elongate torqueable tube, a needle translatably disposed within the torqueable tube, an anchor translatably disposed within the needle and a stabilization device for holding a distal tip of the torqueable tube against a tissue wall.

23 Claims, 9 Drawing Sheets

U.S. PATENT DOCUMENTS

| | | |
|---|---|---|
| 3,874,388 A | 4/1975 | King et al. |
| 3,910,281 A | 10/1975 | Kletschka et al. |
| 3,913,565 A | 10/1975 | Kawahara |
| 3,974,834 A | 8/1976 | Kane |
| 3,976,079 A | 8/1976 | Samuels et al. |
| 4,006,747 A | 2/1977 | Kronenthal et al. |
| 4,007,743 A | 2/1977 | Blake |
| 4,036,218 A | 7/1977 | Yamashita et al. |
| 4,054,128 A | 10/1977 | Seufert et al. |
| 4,060,089 A | 11/1977 | Noiles |
| 4,069,825 A | 1/1978 | Akiyama |
| 4,235,238 A | 11/1980 | Ogiu et al. |
| 4,245,624 A | 1/1981 | Komiya |
| 4,366,810 A | 1/1983 | Slanetz |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,577,621 A | 3/1986 | Patel |
| 4,586,503 A | 5/1986 | Kirsch et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,648,733 A | 3/1987 | Merkt |
| 4,655,257 A | 4/1987 | Iwashita |
| 4,669,473 A | 6/1987 | Richards et al. |
| 4,700,704 A | 10/1987 | Lia et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,790,294 A | 12/1988 | Allred et al. |
| 4,832,055 A | 5/1989 | Palestrant |
| 4,841,888 A | 6/1989 | Mills et al. |
| 4,872,579 A | 10/1989 | Palmer |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsch et al. |
| 4,949,927 A | 8/1990 | Madocks et al. |
| 4,957,498 A | 9/1990 | Caspari et al. |
| 5,005,558 A | 4/1991 | Aomori |
| 5,025,778 A | 6/1991 | Silverstein et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,068,719 A | 11/1991 | Tsuji |
| 5,073,166 A | 12/1991 | Parks et al. |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Guglielmi et al. |
| 5,123,914 A | 6/1992 | Cope |
| RE34,021 E | 8/1992 | Mueller et al. |
| 5,174,276 A | 12/1992 | Crockard |
| 5,176,691 A | 1/1993 | Pierce |
| 5,179,935 A | 1/1993 | Miyagi |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,251,611 A | 10/1993 | Zehel et al. |
| 5,254,126 A | 10/1993 | Filipi et al. |
| 5,261,916 A | 11/1993 | Engelson |
| 5,268,001 A | 12/1993 | Nicholson et al. |
| 5,269,809 A | 12/1993 | Hayhurst et al. |
| 5,271,381 A | 12/1993 | Ailinger et al. |
| 5,282,827 A | 2/1994 | Kensey et al. |
| 5,284,488 A | 2/1994 | Sideris |
| 5,289,817 A | 3/1994 | Williams et al. |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,337,732 A | 8/1994 | Grundfest et al. |
| 5,337,733 A | 8/1994 | Bauerfeind et al. |
| 5,342,376 A | 8/1994 | Ruff |
| 5,345,949 A | 9/1994 | Shlain |
| 5,348,259 A | 9/1994 | Blanco et al. |
| 5,350,399 A | 9/1994 | Erlebacher et al. |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,266 A | 8/1995 | McPherson et al. |
| 5,437,680 A | 8/1995 | Yoon |
| 5,437,681 A | 8/1995 | Meade et al. |
| 5,445,167 A | 8/1995 | Yoon et al. |
| 5,451,235 A | 9/1995 | Lock et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,545,178 A | 8/1996 | Kensey et al. |
| 5,549,618 A | 8/1996 | Fleenor et al. |
| 5,549,621 A | 8/1996 | Bessler et al. |
| 5,558,665 A | 9/1996 | Kieturakis |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |
| 5,571,116 A | 11/1996 | Bolanos et al. |
| 5,571,119 A | 11/1996 | Atala |
| 5,573,496 A | 11/1996 | McPherson et al. |
| 5,573,540 A | 11/1996 | Yoon |
| 5,573,548 A | 11/1996 | Nazre et al. |

| | | | | | | |
|---|---|---|---|---|---|---|
| 5,575,801 A | 11/1996 | Habermeyer et al. | | 5,829,447 A | 11/1998 | Stevens et al. |
| 5,578,045 A | 11/1996 | Das | | 5,836,955 A | 11/1998 | Buelna et al. |
| 5,582,616 A | 12/1996 | Bolduc et al. | | 5,840,078 A | 11/1998 | Yerys |
| 5,584,835 A | 12/1996 | Greenfield | | 5,843,084 A | 12/1998 | Hart et al. |
| 5,584,859 A | 12/1996 | Brotz | | 5,843,126 A | 12/1998 | Jameel |
| 5,591,186 A | 1/1997 | Wurster et al. | | 5,846,261 A | 12/1998 | Kotula et al. |
| 5,601,557 A | 2/1997 | Hayhurst | | 5,855,614 A | 1/1999 | Stevens et al. |
| 5,603,718 A | 2/1997 | Xu | | 5,860,991 A | 1/1999 | Klein et al. |
| 5,613,974 A | 3/1997 | Andreas et al. | | 5,861,003 A | 1/1999 | Latson et al. |
| 5,613,975 A | 3/1997 | Christy | | 5,865,791 A | 2/1999 | Whayne et al. |
| 5,624,381 A | 4/1997 | Kieturakis | | 5,868,760 A | 2/1999 | McGuckin |
| 5,626,588 A | 5/1997 | Sauer et al. | | 5,868,762 A | 2/1999 | Cragg et al. |
| 5,626,614 A | 5/1997 | Hart | | 5,879,371 A | 3/1999 | Gardiner et al. |
| 5,630,540 A | 5/1997 | Blewett | | 5,887,594 A | 3/1999 | LoCicero, III |
| 5,632,752 A | 5/1997 | Buelna | | 5,888,247 A | 3/1999 | Benetti |
| 5,643,274 A | 7/1997 | Sander et al. | | 5,891,168 A | 4/1999 | Thal |
| 5,643,295 A | 7/1997 | Yoon | | 5,893,856 A | 4/1999 | Jacob et al. |
| 5,643,317 A | 7/1997 | Pavcnik et al. | | 5,895,404 A | 4/1999 | Ruiz |
| 5,643,320 A | 7/1997 | Lower et al. | | 5,897,417 A | 4/1999 | Grey |
| 5,653,038 A | 8/1997 | Hunter | | 5,897,562 A | 4/1999 | Bolanos et al. |
| 5,658,312 A | 8/1997 | Green et al. | | 5,899,920 A | 5/1999 | DeSatnick et al. |
| 5,658,313 A | 8/1997 | Thal | | 5,899,921 A | 5/1999 | Caspari et al. |
| 5,662,587 A | 9/1997 | Grundfest et al. | | 5,901,895 A | 5/1999 | Heaton et al. |
| 5,662,654 A | 9/1997 | Thompson | | 5,902,254 A | 5/1999 | Magram |
| 5,662,662 A | 9/1997 | Bishop et al. | | 5,916,147 A | 6/1999 | Boury |
| 5,662,663 A | 9/1997 | Shallman | | 5,916,224 A | 6/1999 | Esplin |
| 5,665,109 A | 9/1997 | Yoon | | 5,921,915 A | 7/1999 | Aznoian et al. |
| 5,665,112 A | 9/1997 | Thal | | 5,925,059 A | 7/1999 | Palermo et al. |
| 5,667,513 A | 9/1997 | Torrie et al. | | 5,928,260 A | 7/1999 | Chin et al. |
| 5,669,917 A | 9/1997 | Sauer et al. | | 5,928,264 A | 7/1999 | Sugarbaker et al. |
| 5,676,670 A * | 10/1997 | Kim .............................. 606/108 | | 5,935,107 A | 8/1999 | Taylor et al. |
| 5,676,674 A | 10/1997 | Bolanos et al. | | 5,941,815 A | 8/1999 | Chang |
| 5,679,005 A | 10/1997 | Einstein | | 5,944,738 A | 8/1999 | Amplatz et al. |
| 5,683,417 A | 11/1997 | Cooper | | 5,947,983 A | 9/1999 | Solar et al. |
| 5,683,419 A | 11/1997 | Thal | | 5,947,997 A | 9/1999 | Pavcnik et al. |
| 5,690,655 A | 11/1997 | Hart et al. | | 5,948,001 A | 9/1999 | Larsen |
| 5,693,060 A | 12/1997 | Martin | | 5,954,731 A | 9/1999 | Yoon |
| 5,700,273 A | 12/1997 | Buelna et al. | | 5,954,732 A | 9/1999 | Hart et al. |
| 5,702,397 A | 12/1997 | Goble et al. | | 5,961,440 A | 10/1999 | Schweich, Jr. et al. |
| 5,702,419 A | 12/1997 | Berry et al. | | 5,964,765 A | 10/1999 | Fenton, Jr. et al. |
| 5,702,421 A | 12/1997 | Schneidt | | 5,964,782 A | 10/1999 | Lafontaine et al. |
| 5,707,394 A | 1/1998 | Miller et al. | | 5,964,783 A | 10/1999 | Grafton et al. |
| 5,709,707 A | 1/1998 | Lock et al. | | 5,971,993 A * | 10/1999 | Hussein et al. ................ 606/108 |
| 5,709,708 A | 1/1998 | Thal | | 5,976,073 A | 11/1999 | Ouchi |
| 5,713,903 A | 2/1998 | Sander et al. | | 5,976,127 A | 11/1999 | Lax |
| 5,720,765 A | 2/1998 | Thal | | 5,976,158 A | 11/1999 | Adams et al. |
| 5,724,978 A | 3/1998 | Tenhoff | | 5,976,159 A | 11/1999 | Bolduc et al. |
| 5,725,552 A | 3/1998 | Kotula et al. | | 5,980,558 A | 11/1999 | Wiley |
| 5,728,045 A | 3/1998 | Komi | | 5,984,933 A | 11/1999 | Yoon |
| 5,732,707 A | 3/1998 | Widder et al. | | 5,993,476 A | 11/1999 | Groiso |
| 5,741,297 A | 4/1998 | Simon | | 6,013,083 A | 1/2000 | Bennett |
| 5,746,752 A | 5/1998 | Burkhart | | 6,017,358 A | 1/2000 | Yoon et al. |
| 5,746,755 A | 5/1998 | Wood et al. | | 6,027,523 A | 2/2000 | Schmieding |
| 5,749,828 A | 5/1998 | Solomon et al. | | 6,033,430 A | 3/2000 | Bonutti |
| 5,749,893 A | 5/1998 | Vidal et al. | | 6,036,699 A | 3/2000 | Andreas et al. |
| 5,752,963 A | 5/1998 | Allard et al. | | 6,042,155 A | 3/2000 | Lockwood |
| 5,759,151 A | 6/1998 | Sturges | | 6,045,497 A | 4/2000 | Schweich, Jr. et al. |
| 5,766,189 A | 6/1998 | Matsuno | | 6,045,573 A | 4/2000 | Wenstrom et al. |
| 5,769,816 A | 6/1998 | Barbut et al. | | 6,050,936 A | 4/2000 | Schweich, Jr. et al. |
| 5,776,150 A | 7/1998 | Nolan et al. | | 6,053,935 A | 4/2000 | Brenneman et al. |
| 5,779,719 A | 7/1998 | Klein et al. | | 6,056,760 A | 5/2000 | Koike et al. |
| 5,782,859 A | 7/1998 | Nicholas et al. | | 6,056,770 A | 5/2000 | Epstein et al. |
| 5,782,865 A | 7/1998 | Grotz | | 6,059,715 A | 5/2000 | Schweich, Jr. et al. |
| 5,787,897 A | 8/1998 | Kieturakis | | 6,059,719 A | 5/2000 | Yamamoto et al. |
| 5,792,152 A | 8/1998 | Klein et al. | | 6,074,401 A | 6/2000 | Gardiner et al. |
| 5,792,153 A | 8/1998 | Swain et al. | | 6,077,214 A | 6/2000 | Mortier et al. |
| 5,797,929 A | 8/1998 | Andreas et al. | | 6,077,281 A | 6/2000 | Das |
| 5,797,960 A | 8/1998 | Stevens et al. | | 6,077,291 A | 6/2000 | Das |
| 5,810,849 A | 9/1998 | Kontos | | 6,079,414 A | 6/2000 | Roth |
| 5,810,851 A | 9/1998 | Yoon | | 6,086,600 A | 7/2000 | Kortenbach |
| 5,810,853 A | 9/1998 | Yoon | | 6,086,601 A | 7/2000 | Yoon |
| 5,810,882 A | 9/1998 | Bolduc et al. | | 6,110,183 A | 8/2000 | Cope |
| 5,814,064 A | 9/1998 | Daniel et al. | | 6,113,609 A | 9/2000 | Adams |
| 5,814,070 A | 9/1998 | Borzone et al. | | 6,113,611 A | 9/2000 | Allen et al. |
| 5,817,107 A | 10/1998 | Schaller | | 6,119,913 A | 9/2000 | Adams et al. |
| 5,817,110 A | 10/1998 | Kronner | | 6,149,658 A | 11/2000 | Gardiner et al. |
| 5,823,956 A | 10/1998 | Roth et al. | | 6,152,935 A | 11/2000 | Kammerer et al. |
| 5,824,011 A | 10/1998 | Stone et al. | | 6,152,946 A | 11/2000 | Broome et al. |
| 5,827,298 A | 10/1998 | Hart et al. | | 6,159,146 A | 12/2000 | El Gazayerli |

| | | | | | | |
|---|---|---|---|---|---|---|
| 6,162,168 | A | 12/2000 | Schweich, Jr. et al. | 6,736,828 B1 | 5/2004 | Adams et al. |
| 6,165,119 | A | 12/2000 | Schweich, Jr. et al. | 6,746,460 B2 | 6/2004 | Gannoe et al. |
| 6,165,120 | A | 12/2000 | Schweich, Jr. et al. | 6,755,843 B2 | 6/2004 | Chung et al. |
| 6,167,889 | B1 | 1/2001 | Benetti | 6,761,685 B2 | 7/2004 | Adams et al. |
| 6,171,320 | B1 | 1/2001 | Monassevitch | 6,773,440 B2 | 8/2004 | Gannoe et al. |
| 6,174,323 | B1 | 1/2001 | Biggs et al. | 6,773,441 B1 | 8/2004 | Laufer et al. |
| 6,179,195 | B1 | 1/2001 | Adams et al. | 6,800,056 B2 | 10/2004 | Tartaglia et al. |
| 6,179,776 | B1 | 1/2001 | Adams et al. | 6,811,532 B2 | 11/2004 | Ogura et al. |
| 6,183,411 | B1 | 2/2001 | Mortier et al. | 6,821,285 B2 | 11/2004 | Laufer et al. |
| RE37,117 | E | 3/2001 | Palermo | 6,835,199 B2 | 12/2004 | McGuckin, Jr. et al. |
| 6,197,022 | B1 | 3/2001 | Baker | 6,837,846 B2 | 1/2005 | Jaffe et al. |
| 6,214,007 | B1 | 4/2001 | Anderson | 6,837,849 B2 | 1/2005 | Ogura et al. |
| 6,214,028 | B1 | 4/2001 | Yoon et al. | 6,921,378 B2 * | 7/2005 | O'Keefe et al. .................. 604/9 |
| 6,221,084 | B1 | 4/2001 | Fleenor | 6,932,834 B2 | 8/2005 | Lizardi et al. |
| 6,228,023 | B1 | 5/2001 | Zaslavsky et al. | 6,955,657 B1 * | 10/2005 | Webler ...................... 604/95.04 |
| 6,231,561 | B1 | 5/2001 | Frazier et al. | 6,986,781 B2 | 1/2006 | Smith |
| 6,238,412 | B1 | 5/2001 | Dubrul et al. | 6,994,717 B2 | 2/2006 | Kónya et al. |
| 6,245,079 | B1 | 6/2001 | Nobles et al. | 6,997,931 B2 | 2/2006 | Sauer et al. |
| 6,260,552 | B1 | 7/2001 | Mortier et al. | 7,063,630 B2 | 6/2006 | Cavallaro |
| 6,261,222 | B1 | 7/2001 | Schweich, Jr. et al. | 7,083,630 B2 | 8/2006 | DeVries et al. |
| 6,264,602 | B1 | 7/2001 | Mortier et al. | 7,131,980 B1 | 11/2006 | Field et al. |
| 6,270,515 | B1 | 8/2001 | Linden et al. | 7,160,312 B2 | 1/2007 | Saadat |
| 6,283,973 | B1 | 9/2001 | Hubbard et al. | 7,186,262 B2 | 3/2007 | Saadat |
| 6,287,315 | B1 | 9/2001 | Wijeratne et al. | 7,416,554 B2 | 8/2008 | Lam et al. |
| 6,290,674 | B1 | 9/2001 | Roue et al. | 2001/0000040 A1 | 3/2001 | Adams et al. |
| 6,293,956 | B1 | 9/2001 | Crainich et al. | 2001/0016675 A1 | 8/2001 | Mortier et al. |
| 6,296,656 | B1 | 10/2001 | Bolduc et al. | 2001/0025171 A1 | 9/2001 | Mortier et al. |
| 6,306,159 | B1 | 10/2001 | Schwartz et al. | 2001/0049509 A1 | 12/2001 | Sekine et al. |
| 6,306,163 | B1 | 10/2001 | Fitz | 2001/0051815 A1 | 12/2001 | Esplin |
| 6,312,437 | B1 | 11/2001 | Kortenbach | 2001/0056282 A1 | 12/2001 | Sonnenschein et al. |
| 6,315,789 | B1 | 11/2001 | Cragg | 2002/0010490 A1 | 1/2002 | Schaller et al. |
| 6,322,563 | B1 | 11/2001 | Cummings et al. | 2002/0013608 A1 | 1/2002 | ElAttrache et al. |
| 6,322,580 | B1 | 11/2001 | Kanner | 2002/0019649 A1 | 2/2002 | Sikora et al. |
| 6,332,468 | B1 | 12/2001 | Benetti | 2002/0022851 A1 | 2/2002 | Kalloo et al. |
| 6,332,863 | B1 | 12/2001 | Schweich, Jr. et al. | 2002/0029080 A1 | 3/2002 | Mortier et al. |
| 6,332,864 | B1 | 12/2001 | Schweich, Jr. et al. | 2002/0040226 A1 | 4/2002 | Laufer et al. |
| 6,332,893 | B1 | 12/2001 | Mortier et al. | 2002/0055689 A1 | 5/2002 | Kaplan et al. |
| 6,336,940 | B1 | 1/2002 | Graf et al. | 2002/0055757 A1 | 5/2002 | Torre et al. |
| 6,346,074 | B1 | 2/2002 | Roth | 2002/0058855 A1 | 5/2002 | Schweich, Jr. et al. |
| 6,348,064 | B1 | 2/2002 | Kanner | 2002/0058905 A1 * | 5/2002 | Madrid et al. .................. 604/43 |
| 6,352,503 | B1 | 3/2002 | Matsui et al. | 2002/0062062 A1 | 5/2002 | Belson et al. |
| 6,355,052 | B1 | 3/2002 | Neuss et al. | 2002/0065534 A1 | 5/2002 | Hermann et al. |
| 6,358,197 | B1 | 3/2002 | Silverman et al. | 2002/0068849 A1 | 6/2002 | Schweich, Jr. et al. |
| 6,363,938 | B2 | 4/2002 | Saadat et al. | 2002/0068945 A1 | 6/2002 | Sixto, Jr. et al. |
| 6,368,338 | B1 | 4/2002 | Kónya et al. | 2002/0072761 A1 | 6/2002 | Abrams et al. |
| 6,368,339 | B1 | 4/2002 | Amplatz | 2002/0077524 A1 | 6/2002 | Schweich, Jr. et al. |
| 6,387,104 | B1 | 5/2002 | Pugsley, Jr. et al. | 2002/0078967 A1 | 6/2002 | Sixto, Jr. et al. |
| 6,391,044 | B1 | 5/2002 | Yadav et al. | 2002/0082621 A1 | 6/2002 | Schurr et al. |
| 6,402,679 | B1 | 6/2002 | Mortier et al. | 2002/0082622 A1 | 6/2002 | Kane |
| 6,402,680 | B2 | 6/2002 | Mortier et al. | 2002/0087098 A1 * | 7/2002 | Iwami et al. .................. 600/585 |
| 6,406,420 | B1 | 6/2002 | McCarthy et al. | 2002/0107530 A1 | 8/2002 | Sauer et al. |
| H2037 | H | 7/2002 | Yates et al. | 2002/0111534 A1 | 8/2002 | Suzuki et al. |
| 6,423,087 | B1 | 7/2002 | Sawada | 2002/0116012 A1 | 8/2002 | May et al. |
| 6,425,859 | B1 | 7/2002 | Foley et al. | 2002/0120178 A1 | 8/2002 | Tartaglia et al. |
| 6,425,911 | B1 | 7/2002 | Akerfeldt et al. | 2002/0147385 A1 | 10/2002 | Butler et al. |
| 6,447,533 | B1 | 9/2002 | Adams et al. | 2002/0161281 A1 | 10/2002 | Jaffe et al. |
| 6,494,888 | B1 | 12/2002 | Laufer et al. | 2002/0183768 A1 | 12/2002 | Deem et al. |
| 6,505,190 | B1 | 1/2003 | Harel et al. | 2002/0193661 A1 | 12/2002 | Belson |
| 6,506,196 | B1 | 1/2003 | Laufer | 2002/0193662 A1 | 12/2002 | Belson |
| 6,508,828 | B1 | 1/2003 | Akerfeldt et al. | 2002/0193816 A1 | 12/2002 | Laufer et al. |
| 6,533,796 | B1 | 3/2003 | Sauer et al. | 2002/0198537 A1 | 12/2002 | Smith et al. |
| 6,537,285 | B1 | 3/2003 | Hatasaka, Jr. et al. | 2003/0009085 A1 | 1/2003 | Arai et al. |
| 6,554,793 | B1 | 4/2003 | Pauker et al. | 2003/0045778 A1 | 3/2003 | Ohline et al. |
| 6,554,845 | B1 | 4/2003 | Fleenor et al. | 2003/0055442 A1 | 3/2003 | Laufer et al. |
| 6,558,400 | B2 | 5/2003 | Deem et al. | 2003/0065359 A1 | 4/2003 | Weller et al. |
| 6,569,085 | B2 | 5/2003 | Kortenbach et al. | 2003/0109892 A1 | 6/2003 | Deem et al. |
| 6,572,629 | B2 | 6/2003 | Kalloo et al. | 2003/0109900 A1 | 6/2003 | Martinek |
| 6,589,208 | B2 | 7/2003 | Ewers et al. | 2003/0120289 A1 | 6/2003 | McGuckin et al. |
| 6,641,592 | B1 | 11/2003 | Sauer et al. | 2003/0130693 A1 | 7/2003 | Levin et al. |
| 6,656,182 | B1 * | 12/2003 | Hayhurst ...................... 606/72 | 2003/0139752 A1 | 7/2003 | Pasricha et al. |
| 6,656,194 | B1 | 12/2003 | Gannoe et al. | 2003/0158582 A1 | 8/2003 | Bonutti et al. |
| 6,663,639 | B1 | 12/2003 | Laufer et al. | 2003/0165887 A1 | 9/2003 | Reed |
| 6,669,707 | B1 | 12/2003 | Swanstrom et al. | 2003/0167062 A1 | 9/2003 | Gambale et al. |
| 6,695,764 | B2 | 2/2004 | Silverman et al. | 2003/0167071 A1 * | 9/2003 | Martin et al. .................. 606/232 |
| 6,699,263 | B2 | 3/2004 | Cope | 2003/0171651 A1 | 9/2003 | Page et al. |
| 6,702,826 | B2 | 3/2004 | Liddicoat et al. | 2003/0171760 A1 | 9/2003 | Gambale |
| 6,716,232 | B1 | 4/2004 | Vidal et al. | 2003/0176890 A1 | 9/2003 | Buckman et al. |
| 6,719,763 | B2 | 4/2004 | Chung et al. | 2003/0181924 A1 | 9/2003 | Yamamoto et al. |
| 6,719,764 | B1 | 4/2004 | Gellman et al. | 2003/0204205 A1 | 10/2003 | Sauer et al. |

| | | |
|---|---|---|
| 2003/0240205 | 10/2003 | Sauer et al. |
| 2003/0208209 A1 | 11/2003 | Gambale et al. |
| 2003/0208211 A1* | 11/2003 | Kortenbach .................. 606/151 |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236505 A1 | 12/2003 | Bonadio et al. |
| 2003/0236536 A1 | 12/2003 | Grigoryants et al. |
| 2003/0236549 A1 | 12/2003 | Bonadio et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0097986 A1 | 5/2004 | Adams |
| 2004/0116949 A1 | 6/2004 | Ewers et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0122474 A1 | 6/2004 | Gellman et al. |
| 2004/0133238 A1 | 7/2004 | Cerier |
| 2004/0138682 A1 | 7/2004 | Onuki et al. |
| 2004/0147941 A1 | 7/2004 | Takemoto et al. |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0176784 A1 | 9/2004 | Okada |
| 2004/0193008 A1 | 9/2004 | Jaffe et al. |
| 2004/0193009 A1 | 9/2004 | Jaffe et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1 | 10/2004 | Laufer et al. |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2004/0249392 A1 | 12/2004 | Mikkaichi et al. |
| 2004/0249395 A1 | 12/2004 | Mikkaichi et al. |
| 2005/0004576 A1 | 1/2005 | Benderev |
| 2005/0020901 A1 | 1/2005 | Belson et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0070931 A1 | 3/2005 | Li et al. |
| 2005/0075653 A1 | 4/2005 | Saadat et al. |
| 2005/0113640 A1 | 5/2005 | Saadat et al. |
| 2005/0119671 A1 | 6/2005 | Reydel et al. |
| 2005/0149115 A1 | 7/2005 | Roue et al. |
| 2005/0192629 A1 | 9/2005 | Saadat et al. |
| 2005/0203488 A1 | 9/2005 | Michlitsch et al. |
| 2005/0203489 A1 | 9/2005 | Saadat et al. |
| 2005/0203500 A1 | 9/2005 | Saadat et al. |
| 2005/0234294 A1 | 10/2005 | Saadat et al. |
| 2005/0234296 A1 | 10/2005 | Saadat et al. |
| 2005/0245945 A1* | 11/2005 | Ewers et al. .................. 606/153 |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251209 A1 | 11/2005 | Saadat et al. |
| 2005/0251210 A1 | 11/2005 | Westra et al. |
| 2005/0267523 A1 | 12/2005 | Devellian et al. |
| 2005/0272977 A1 | 12/2005 | Saadat et al. |
| 2005/0273135 A1 | 12/2005 | Chanduszko et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0100579 A1 | 5/2006 | Maahs et al. |
| 2006/0135971 A1 | 6/2006 | Swanstrom et al. |
| 2006/0157067 A1 | 7/2006 | Saadat et al. |
| 2006/0161185 A1 | 7/2006 | Saadat et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |
| 2006/0217762 A1 | 9/2006 | Maahs et al. |
| 2006/0237022 A1 | 10/2006 | Chen et al. |
| 2006/0237023 A1 | 10/2006 | Cox et al. |
| 2006/0241661 A1 | 10/2006 | DeVries et al. |
| 2006/0258909 A1 | 11/2006 | Saadat et al. |
| 2006/0271073 A1 | 11/2006 | Lam et al. |
| 2006/0271074 A1 | 11/2006 | Ewers et al. |
| 2006/0271101 A1 | 11/2006 | Saadat et al. |
| 2007/0123840 A1 | 5/2007 | Cox |
| 2007/0142849 A1 | 6/2007 | Ewers et al. |

FOREIGN PATENT DOCUMENTS

| | | |
|---|---|---|
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO02/30335 | 4/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A1 | 11/2003 |

| | | |
|---|---|---|
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/075787 A1 | 9/2004 |
| WO | WO 2004/084808 A2 | 10/2004 |
| WO | WO 2004/103189 A1 | 12/2004 |
| WO | WO 2005/004727 A1 | 1/2005 |
| WO | WO 2005/037072 A2 | 4/2005 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, (Jul. 1987), pp. 772-776.

Brolin et al., Experimental Evaluation of Techniques of Gastric Paritioning for Morbid Obesity, Surgery, Gynecology & Obstetrics, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, (Oct. 1984), pp. 564-568.

Surgical Dynamics Inc., The S•D•sorb Meniscal Stapler [brochure] (1997), 3 pages total.

Sutura, The Next Generation in Vascular Suturing Devices: SuperStitch [brochure], 2 pages total.

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.

Mason, "Development of Future of Gastroplasties for Morbid Obesity," *Arch Surg*, vol. 138 (Apr. 2003), pp. 362-366.

File History for European Patent Application No. 3817830.7 filed Dec. 22, 2003.

Supplemental Search Report for European Patent Application No. 3817830.7 filed Dec. 22, 2003.

International Search Report for PCT International Application No. PCT/US2003/034726 filed Oct. 31, 2003.

International Search Report for PCT International Application No. PCT/US2003/040859 filed Dec. 22, 2003.

International Search Report for PCT International Application No. PCT/US2004/041570 filed Dec. 10, 2004.

International Preliminary Report on Patentability for PCT International Patent Application No. PCT/US2004/041570 filed Dec. 10, 2004.

File History for U.S. Appl. No. 10/612,170, filed Jul. 1, 2003.
File History for U.S. Appl. No. 10/612,491, filed Jul. 1, 2003.
File History for U.S. Appl. No. 10/639,162, filed Aug. 11, 2003.
File History for U.S. Appl. No. 10/672,375, filed Sep. 25, 2003
File History for U.S. Appl. No. 10/734,547, filed Dec. 12, 2003.
File History for U.S. Appl. No. 10/734,562, filed Dec. 12, 2003.
File History for U.S. Appl. No. 10/735,030, filed Dec. 12, 2003.
File History for U.S. Appl. No. 10/992,306, filed Nov. 17, 2004.
File History for U.S. Appl. No. 10/992,912, filed Nov. 18, 2004.
File History for U.S. Appl. No. 10/994,101, filed Nov. 18, 2004.

* cited by examiner

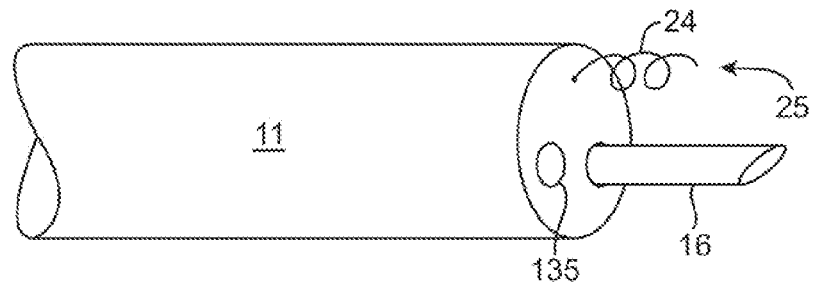
FIG. 15A
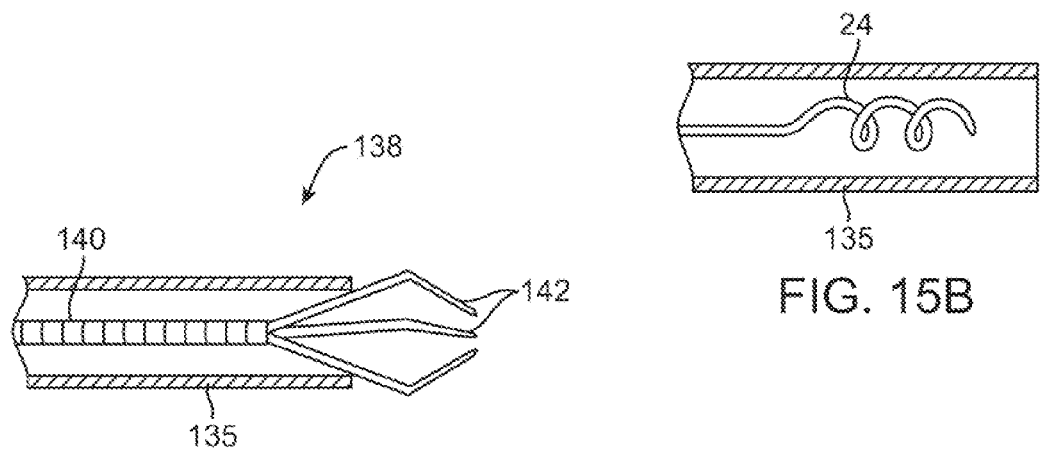
FIG. 15B
FIG. 16
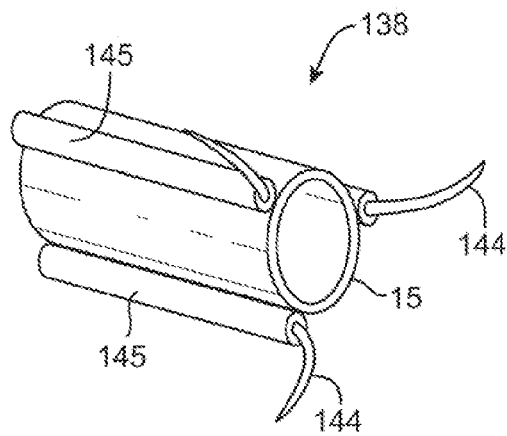
FIG. 17A
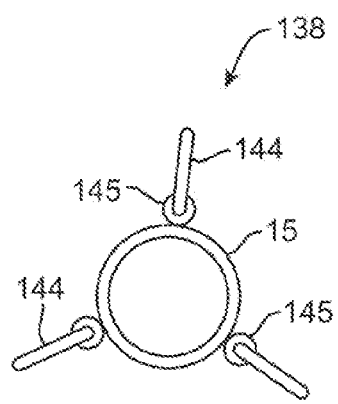
FIG. 17B

DELIVERY SYSTEMS AND METHODS FOR GASTRIC REDUCTION

REFERENCE TO RELATED APPLICATIONS

This application claims priority from U.S. Provisional Patent Application No. 60/433,065, filed Dec. 11, 2002, which is incorporated herein by reference in its entirety.

FIELD OF THE INVENTION

The present invention relates to methods and apparatus for reducing the effective cross-sectional area of a gastro-intestinal ("GI") lumen.

BACKGROUND OF THE INVENTION

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length.

In addition, previously known open surgical procedures may present numerous life-threatening postoperative complications, and may cause a typical diarrhea, electrolytic imbalance, unpredictable weight loss and reflux of nutritious chyme proximal to the site of the anastamosis. Further, the sutures or staples that are often used in these surgical procedures may require extensive training by the clinician to achieve competent use, and may concentrate significant force over a small surface area of the tissue, thereby potentially causing the suture or staple to tear through the tissue.

In view of the aforementioned limitations, it would be desirable to provide methods and apparatus for achieving gastric reduction by reconfiguring the GI lumen of a patient.

It also would be desirable to provide methods and apparatus for gastric reduction including various end effectors that facilitate gastric reduction.

It further would be desirable to provide methods and apparatus for gastric reduction using a delivery catheter having an obturator that facilitates delivery of biocompatible anchors.

It further would be desirable to provide methods and apparatus for gastric reduction using a delivery catheter having an ejection needle capable of housing and placing a plurality of anchors sequentially.

SUMMARY OF THE INVENTION

In view of the foregoing, it is an object of the present invention to provide methods and apparatus for gastric reduction having various end effectors that facilitate gastric reduction.

It is another object of the present invention to provide methods and apparatus for gastric reduction using anchors that can be reconfigured from a reduced delivery profile to an expanded deployed profile.

It is an additional object of this invention to provide methods and apparatus for gastric reduction using a delivery catheter having an obturator that facilitates delivery of biocompatible anchors.

It is a further object of the present invention to provide methods and apparatus for gastric reduction using a delivery catheter having an ejection needle capable of housing and placing a plurality of anchors sequentially.

These and other aspects of the present invention are accomplished by providing a gastric reduction system including methods and apparatus for delivering a plurality of anchors on opposing sides of a gastro-intestinal lumen and then moving the anchors to approximate the opposing walls of the lumen.

One aspect of the present invention involves using a delivery catheter to narrow a cross-sectional area of a gastrointestinal lumen. The delivery catheter comprises an elongate torqueable tube, a needle translatably disposed within the torqueable tube and an anchor translatably disposed within the needle. The delivery catheter may include a stabilization device such as a coil screw to facilitate anchor delivery. According to some embodiments, the coil screw is fixedly attached to a distal end of the torqueable tube and the individual coils form a central opening for the passage of the needle. In another embodiment, the coil screw is translatably disposed within a delivery catheter lumen.

In a further embodiment, the stabilization device comprises a shaft coupled to a plurality of resilient fingers and disposed within a delivery catheter lumen. The resilient fingers are adapted to automatically expand into a deployed configuration upon exiting the delivery catheter. Alternatively, the stabilization device comprises a plurality of resilient wires disposed within lumens spaced apart around the periphery of the torqueable tube. The resilient wires preferably are curved such that they extend radially outward from the distal tip of the torqueable tube when in a deployed configuration.

In still further embodiments, the needle is curved such that initial deployment of the needle through the coil screw causes the needle to penetrate the tissue wall such that a distal tip of the needle moves from a first side of the tissue wall to a second side of the tissue wall. Further deployment of the needle through the coil screw causes the needle to penetrate the tissue wall for a second time such that the distal tip of the needle moves from the second side of the tissue wall back to the first side of the tissue wall. The anchor then is ejected through the needle after the distal tip of the needle penetrates the tissue wall for the second time.

According to another aspect of the present invention, the delivery catheter includes an obturator comprising an elongate shaft translatably disposed within the torqueable tube. Advantageously, a plurality of anchors may be disposed about the shaft of the obturator. The obturator includes a sharpened distal tip adapted to be extended beyond the distal end of the torqueable tube to facilitate the penetration of tissue wall. Alternatively, the obturator may have a blunt, spring-loaded tip extending distally from a sharpened distal tip so that the blunt, spring-loaded tip extends beyond the sharpened distal tip after the tip penetrates within a cavity.

According to a further aspect of the present invention, the delivery catheter comprises an ejection needle having an actuator cable, a first lumen housing a plurality of anchors, a second lumen and a spring-loaded shifting element for shifting the anchors from the first lumen to the second lumen. Pulling the actuator cable in a proximal direction causes an anchor to be shifted from the first lumen to the second lumen. The delivery catheter further comprises a push rod for ejecting the anchor from the ejection lumen.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 15A and 15B are perspective and sectional views, respectively, of alternative delivery catheters of the present invention;

FIG. 16 is a sectional view of an alternative stabilizing device of the present invention;

FIGS. 17A and 17B are perspective views of an alternative stabilizing device of the present invention;

DETAILED DESCRIPTION OF THE INVENTION

Figure 1:
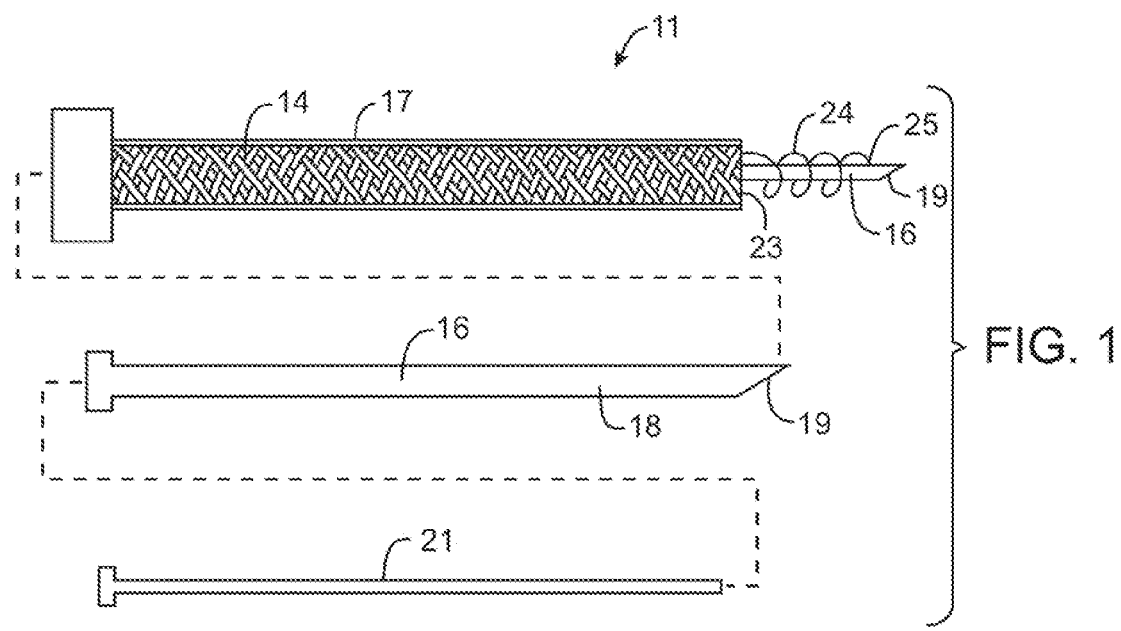
FIG. 1 is a schematic view of an illustrative delivery catheter for use with the gastric reduction methods of the present invention.

Overview of a Preferred Gastric Reduction System

Referring to FIGS. 1-7, illustrative components of gastric reduction apparatus 10 in accordance with the principles of the present invention are described. As explained in detail hereinafter, apparatus 10 enables a clinician to treat obesity by approximating the walls of a gastro-intestinal lumen to narrow the lumen, thus reducing the area for absorption in the stomach or intestines. Gastric reduction system 10 comprises anchor delivery catheter 11, anchor 22, and suture tensioning assembly 50. The structure and operation of each of these components are described separately below.

A. Delivery Catheter

Figure 2:
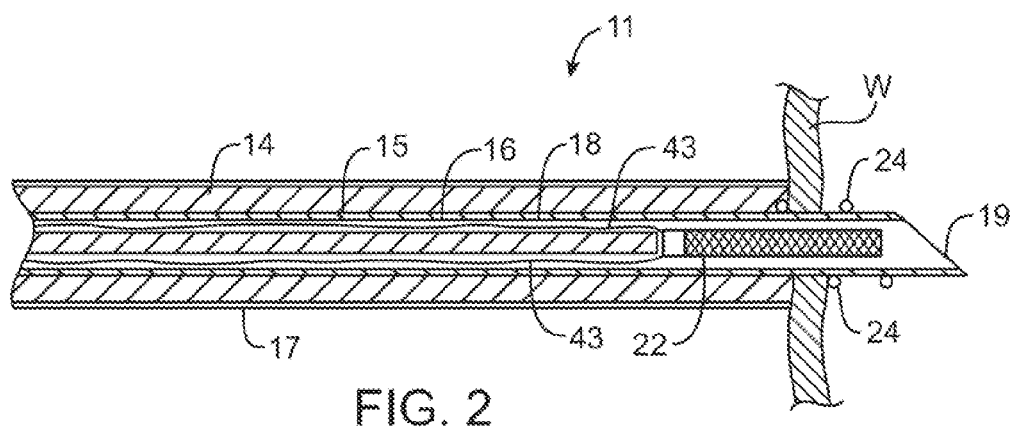
FIG. 2 is a side-sectional view of the delivery catheter of FIG. 1, loaded with an anchor of the present invention, penetrating a GI tissue wall of a patient.

Referring now to FIGS. 1 and 2, an illustrative embodiment of delivery catheter 11 constructed in accordance with the principles of the present invention is described. Delivery catheter 11 comprises elongate torqueable tube 14 having lumen 15 and needle 16 disposed for translation within lumen 15. Torqueable tube 14 preferably is formed of braided stainless steel wire having TEFLON coating 17. Needle 16 includes lumen 18 and non-coring distal tip 19 that facilitates penetration of tissue wall W. Needle 16 preferably is configured to penetrate tissue wall W so that the tissue anchor, described below, may employ a substantially atraumatic distal tip.

Push rod 21 is disposed for translation within lumen 18, and is configured to eject anchor 22 (see FIG. 2) out of distal end 23 of the delivery catheter and through tissue wall W. Referring to FIG. 2, one or more sutures 43 are attached to anchor 22, and extend through lumen 18 of needle 16 so that the proximal ends of the sutures 43 extend out of the mouth of the patient.

To facilitate penetration of needle 16 into tissue wall W, delivery catheter 11 preferably includes a stabilization device in the form of coil 24 that may be engaged to tissue wall W to stabilize distal end 23 of delivery catheter 11 against the tissue during actuation of needle 16. Coil 24 preferably is attached at one end to distal end 23 of catheter 11 and terminates at the other end in sharpened tip 25. According to some embodiments, coil 24 and needle are coaxial such that coil 24 defines a central passage that permits needle 16 to be reciprocated therethrough.

Figure 3:
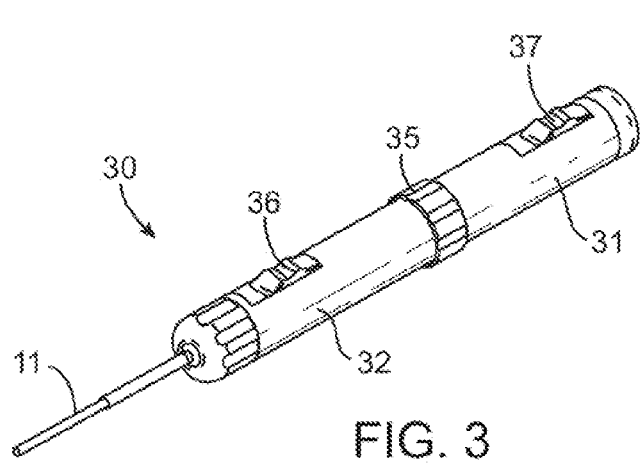
FIG. 3 is a perspective view of the handle of the catheter of FIGS. 1 and 2.

Referring to FIG. 3, an illustrative handle 30 for controlling operation of delivery catheter 11 is described. Handle 30 comprises proximal portion 31 and distal portion 32. Distal portion 32 is coupled to elongate tube 14 so that rotation of knob 35 rotates coil 24 to engage wall W of the gastro-intestinal tissue, as illustrated in FIG. 2. Handle 30 further comprises slider buttons 36 and 37 for imparting translational movement to needle 16 and push rod 21, respectively.

In operation, after knob 35 has been rotated to engage coil 24 to tissue wall W, slider button 36 is actuated to urge needle 16 distally to pass through coil 24 and penetrate wall W. Once needle tip 19 has penetrated the tissue wall, slider button 37 is actuated urge push rod 21 distally, thus ejecting anchor 22 from needle 16 on the distal side of tissue wall W. After the anchor assembly has been deployed, slider buttons 36 and 37 are retracted in the proximal direction to retract the needle and push rod back within elongate tube 14. Knob 35 may then be rotated in the opposite direction to release its engagement with tissue wall W.

B. Anchor

Figure 4A:
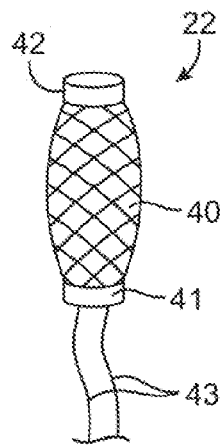
FIGS. 4A and 4B are views of one preferred embodiment of an anchor of the present invention in the reduced delivery state.
Figure 4B:
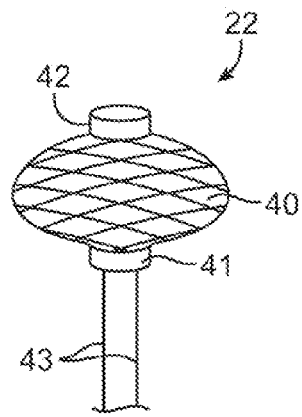

Referring now to FIGS. 4A and 4B, a preferred embodiment of anchor 22 constructed in accordance with the principles of the present invention is described. Anchor 22 comprises braided sleeve 40 coupled to proximal bushing 41 and distal bushing 42. One or more sutures 43 are coupled to distal bushing 42 and extend through bushing 41. Proximal bushing 41 may slide along the suture(s) relative to the distal bushing 42, so that braided sleeve expands radially outward. Accordingly, after anchor 22 is disposed through a tissue wall (as depicted in FIG. 2), application of tension to the sutures causes the anchor to transition from an elongate reduced delivery profile (FIG. 4a) to an expanded, substantially disk-shaped deployed profile (FIG. 4B).

Braided sleeve 40 preferably comprises a highly porous, compliant and high strength material composed of numerous individual monofilament elements. Suitable materials for the monofilament elements include polyester, nylon, TEFLON, polypropylene and combinations thereof. Braided sleeve 40 also may be formed from a shape memory metal, such as a Nickel-Titanium alloy. In addition, the porous braid structure may promote an easily and uniformly absorbable structure for use in applications in which anchor 22 is not intended for permanent implantation. Conversely, the porous braid structure may promote tissue growth to enhance anchoring in applications in which anchor 22 is designed for permanent implantation.

Anchor 22 may be made by thermo-forming two ends of a short length of braided sleeve to form proximal and distal bushings 41 and 42. Alternatively, separate bushings may be glued, over-molded, soldered or welded onto the ends of a length of braided sleeve. Suture(s) 43 may be attached to distal bushing 42 at a fixture point comprising, for example, one or more holes 46 formed in the distal bushing. Alternatively, the sutures may be attached using an eyelet, adhesive or other suitable fastener.

Figure 5A:
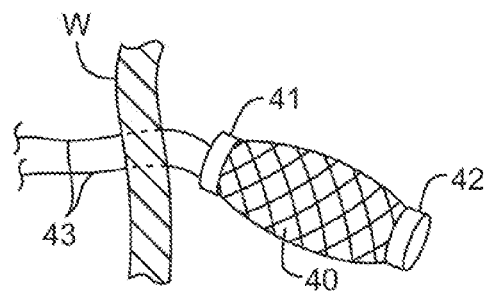
FIGS. 5A-5C are side views depicting transmural implantation of the anchor assembly of FIGS. 4A-4B.
Figure 5B:
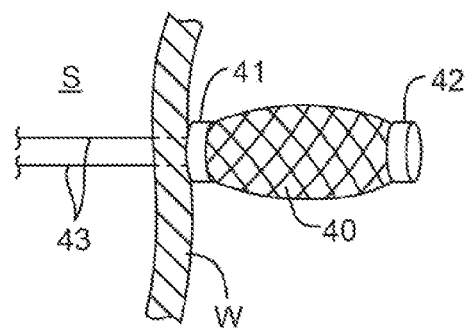
Figure 5C:
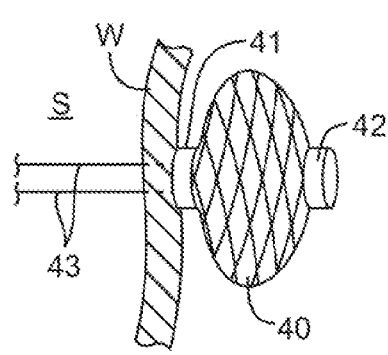

FIGS. 5A-5C depict deployment of anchor 22 from the reduced delivery profile to the expanded deployed profile. In FIG. 5A, anchor 22 has been forced through tissue wall W, illustratively the stomach wall, via needle lumen 18. Once delivery catheter 11 is withdrawn, anchor 22 is left disposed through tissue wall W with untensioned sutures 43 extending into the patient's stomach S. Sutures 43 pass through the esophagus and extend from the patient's mouth where they may be manipulated by the clinician.

In FIG. 5B, sutures 43 are shown partially tensioned, so that proximal bushing 41 engages the distal surface of tissue wall W. Because the stomach wall comprises a tough, resilient material, contact between the expanded braided sleeve and distal surface of the tissue wall causes the braided sleeve to partially expand, rather than slip back into the stomach via the track left by needle 16. When further tension is applied to sutures 43, distal bushing 42 is approximated toward proximal bushing 41, thereby causing braided sleeve 40 to expand in the radially to the substantially disk-shaped profile shown in FIG. 5C.

Alternatively, anchor 22 may be preformed to self-expand to disk-shaped profile to automatically upon ejection from lumen 18 of needle 16. Such a preset shape may be accomplished by coupling the anchor to a fixture (e.g., a mandrel) and heat setting the braided sleeve in the disk-shaped profile. For example, the bushings may be approximated and then retained in close proximity by a fixture, or the shape may be imposed by compressing the braid in a disk-shaped mold. The formed anchor and fixture then may be placed into an oven for a predetermined amount of time, and quenched or slowly cooled to room temperature.

C. Suture Tensioning Assembly

Figure 6:
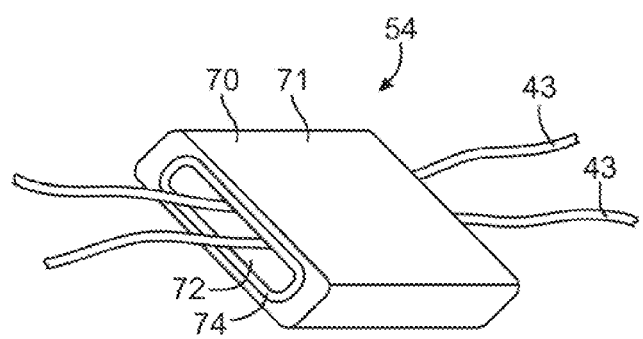
FIG. 6 is a perspective view of a fastener suitable for use with the anchors of the present invention.

Referring now to FIG. 6, illustrative suture fastener 54 constructed in accordance with the principles of the present invention is described. Fastener 54 comprises collar 70 having body 71 and channel 72 through which sutures 43 may freely translate prior to crimping. Once fastener 54 is crimped, sutures 43 are restrained from further translation through channel 72, thus retaining a desired amount of tension on sutures 43. Optionally, body 71 may incorporate lining 74 to enhance friction between body 71 and suture 43, thereby reducing the risk of slippage.

Figure 7A:
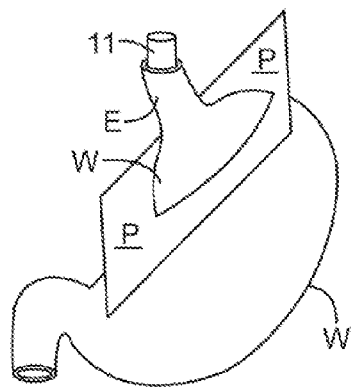
FIGS. 7A-7E are cross-sectional views depicting methods of using the gastric reduction system of the present invention.

FIGS. 7A to 7E illustrate the steps of one procedure using gastric reduction system 10 to treat obesity. In FIG. 7A delivery catheter 11 of FIGS. 1-3 is inserted through a patient's mouth, esophagus E and stomach S. FIGS. 7B-7E depict cross-sectional views of the stomach taken along plane P of FIG. 7A.

Figure 7B:
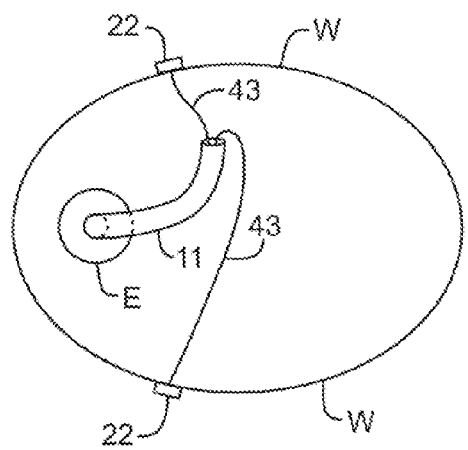
Figure 7C:
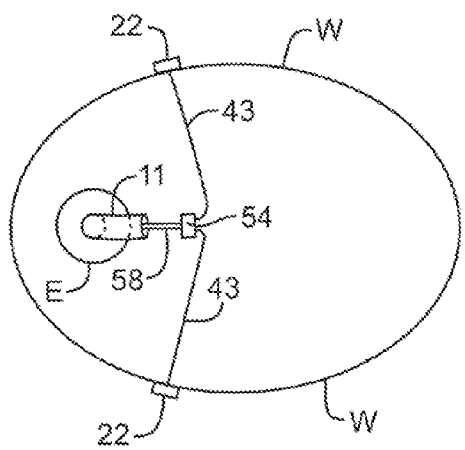

FIG. 7B depicts a step in the which a pair of anchors 22 have been positioned through opposing tissue walls W of the stomach so that sutures 43 pass from each anchor through esophagus E and extend out of the patient's mouth. FIG. 7C depicts a step in which sutures 43 have been threaded through the channel of fastener 54. At this point, fastener 54 has not been crimped and may be freely translated along sutures 43 using a push rod. More particularly, tension is maintained in the sutures while push rod 58 is used to urge fastener 54 through patient's mouth and esophagus E and into the stomach.

Figure 7D:
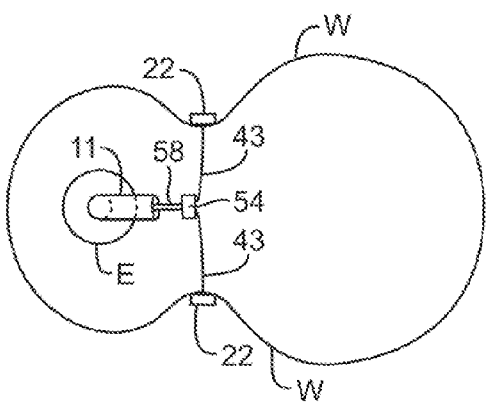
Figure 7E:
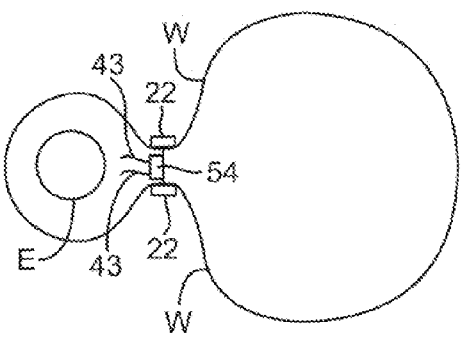

FIG. 7D depicts a step in which fastener 54 is moved to a position approximately midway between anchors 22. Push rod 58 then is used to hold the fastener in place while additional tension is applied to the sutures, thereby causing opposing walls W of the stomach to bow inward toward one another. As depicted in FIG. 7E, the application of additional tension pulls the opposing tissue walls into proximity with each other, thereby narrowing the cross-sectional area of stomach S.

At this step in the procedure, fastener 54 is crimped to maintain the tension in sutures 43. The excess length of sutures 43 is cut and removed via the patient's mouth. Advantageously, narrowing of stomach S limits the amount of food the patient consumes by providing a feeling of satiety after only a small amount of food is ingested.

Alternatively or in addition, sutures 43 may comprise self-tightening materials that shrink over time, or materials such as nickel titanium or electroactive polymers that are pre-stretched so that the subsequent application of heat or electricity causes the sutures to shorten. By way of example, if pre-stretched nickel titanium or electroactive polymeric sutures are used, heat from a radiofrequency device or hot water may be used after the procedure to induce the sutures to tighten. Tension may be controlled by the ability of the sutures to tighten to a specific load. Tension also may be maintained by tying a knot or fusing the sutures to each other via application of heat.

Figure 8:
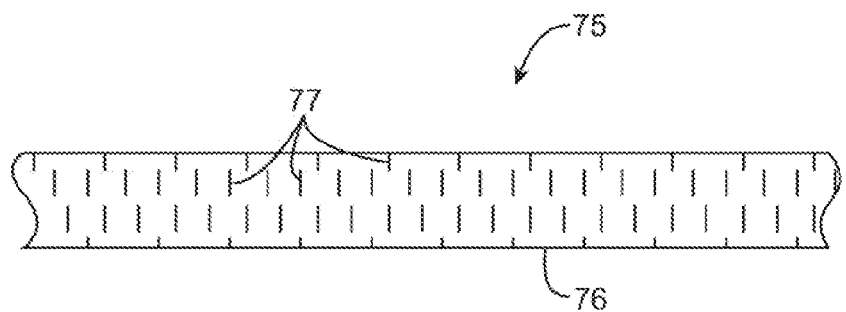
FIG. 8 is a side view of a delivery catheter having a slotted torqueable tube constructed in accordance with the present invention.

Alternative Delivery Catheter Embodiments Suitable for Use With the Gastric Reduction System As described above with respect to FIG. 1, the preferred delivery catheter 11 includes torqueable tube 14 formed of braided stainless steel wire. Referring now to FIG. 8, alternative delivery catheter 75 instead comprises torqueable tube 76 having a plurality of through-wall slots 77 formed therein to enhance flexibility of the tube, yet maintain torqueability. Other components of the delivery catheter, includind needle 16 and push rod 21, may be configured as described hereinabove for the embodiment of FIG. 1.

Preferably, torqueable tube 76 is made from stainless steel with a laser-cut slot pattern. The slot pattern may be a sinusoidal repeating pattern of slots perpendicular to the longitudinal axis of torqueable tube 76. Alternatively, the slot density may be increased near the distal end of torqueable tube to provide a flexible distal tip capable of retroflexing, yet maintain a high degree of torqueability.

Figure 9A:
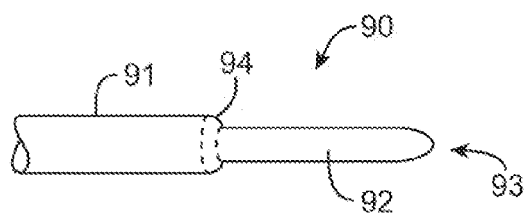
FIGS. 9A-9D are side views of an obturator suitable for use with a delivery catheter of the present invention.
Figure 9B:
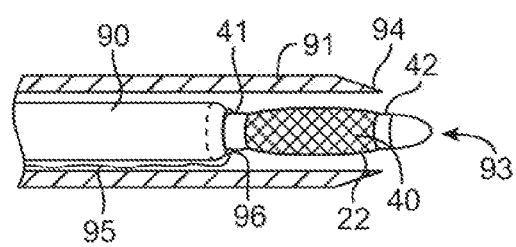
Figure 9C:
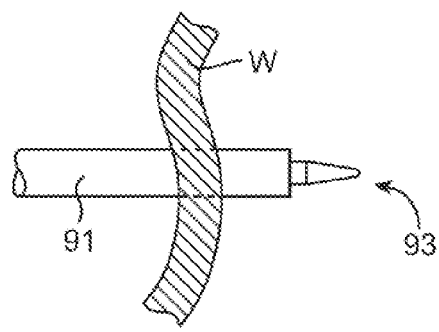

Referring to FIGS. 9A-9D, the anchors of the present invention may be delivered using obturator 90 translatably disposed within a lumen of delivery catheter 91. In FIG. 9A, obturator 90 preferably includes elongated shaft 92 having sharpened distal tip 93 to facilitate tissue penetration. In FIG. 9B, anchor 22 is shown disposed in the reduced delivery profile around obturator shaft 92, with suture 95 attached to the anchor at fixture point 96. Obturator 90 is disposed to reciprocate within the delivery catheter, so that the sharpened distal tip may be extended past the distal tip 94. Because obturator 90 has sharpened distal tip 93, the anchor need not include a sharpened end suitable for penetration.

Figure 9D:
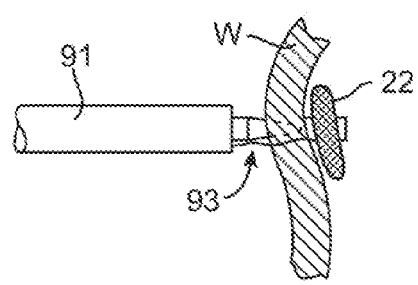

With respect to FIG. 9B, to penetrate tissue wall W, obturator 90 is extended from delivery catheter 91 and until the distal tip of the obturator passes through the tissue wall along with anchor 22. Once the obturator and anchor have passed through tissue wall W, the obturator is retracted (FIG. 9D). At this point, anchor 22 either self-expands to the expanded deployed profile or is induced to expand by applying tension to suture 95. Contact between the expanded anchor and the tissue wall prevents the anchor from being retracted along with the obturator. Tension applied to suture 95 to approximate tissue further reinforces the expanded profile by pulling the bushings together.

Although obturator 90 of FIG. 9 accepts only a single anchor, it will be apparent to one of skill in the art of instrument design that obturator 90 may be configured to accept a plurality of anchors without departing from the scope of the present invention. A push rod (such as push rod 21 of FIG. 1) translatably disposed within delivery catheter 91, and adjacent to the obturator shaft may be used to advance the anchors along the shaft.

Figure 10:
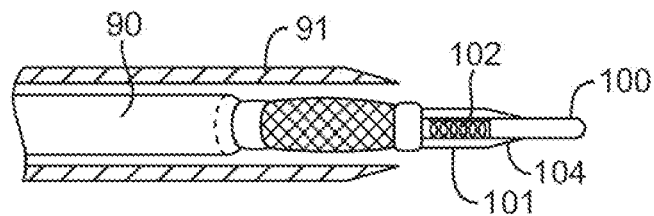
FIG. 10 is a sectional view of an alternative obturator suitable for use with a delivery catheter of the present invention.

Referring now to FIG. 10 and in accordance with an alternative embodiment, obturator 90 includes blunt, spring-loaded distal tip 100. When the obturator is pushed against a tissue wall, blunt tip 100 is depressed within longitudinally disposed cavity 101 containing compression spring 102. Depressing the blunt distal tip also exposes the tissue to sharpened obturator tip 104, which punctures the tissue wall. Once the sharpened tip 104 penetrates the tissue wall, compression spring 102 ejects the blunt tip 100 from cavity 101, thereby shielding surrounding tissue from sharpened tip 104.

Figure 11A:
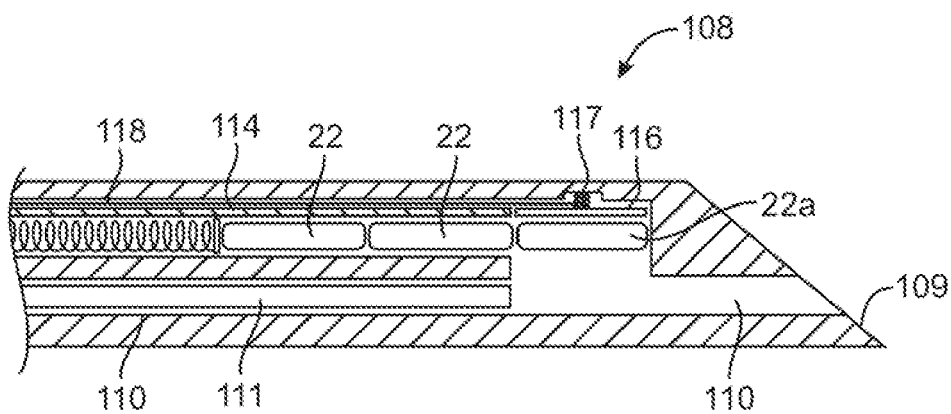
FIGS. 11A and 11B are cross-sectional views of an ejection needle suitable for use with a delivery catheter of the present invention.
Figure 11B:
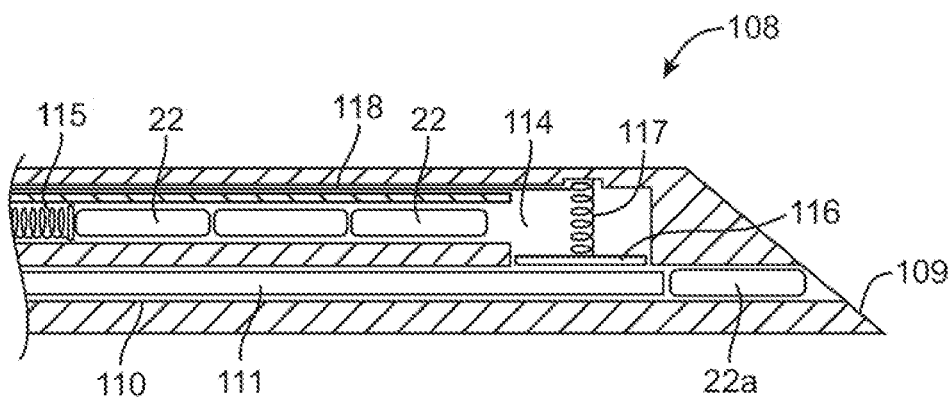

With respect to FIGS. 11A and 11B, an alternative embodiment of an ejection needle suitable for use with the delivery catheter of FIG. 1 and configured to house and deliver a plurality of anchors 22 is described. Ejection needle 108 comprises non-coring distal tip 109, ejection lumen 110 through which push rod 111 is slidably disposed, anchor lumen 114 for storing anchors 22, first compression spring 115 disposed proximally with respect to anchor lumen 114 and spring-loaded shifting element 116 for shifting individual anchors from the anchor lumen to the ejection lumen. Shifting element 116 is coupled to second compression spring 117 that biases the shifting element toward the ejection lumen. In addition, actuator cable 118 extends from the shifting element to a trigger located at the proximal end of catheter 108.

When the trigger is actuated, the actuator cable is pulled proximally. This caused shifting element 116 to overcome the force exerted by compression spring 117 and move away from ejection lumen 110. Retraction of shifting element 116 against compression spring 117 permits anchor 22a to slide distally out of lumen 114 (under the urging of compression spring 115), so that anchor 22a is disposed substantially directly beneath shifting element 116 in the path of push rod 111 (FIG. 11A). When the trigger is released, compression spring 117 forces the shifting element 116 and anchor 22a toward ejection lumen 110. Once the anchor is pushed into ejection lumen 110, push rod 111 is used to eject anchor 22a from distal tip 109.

Figure 12:
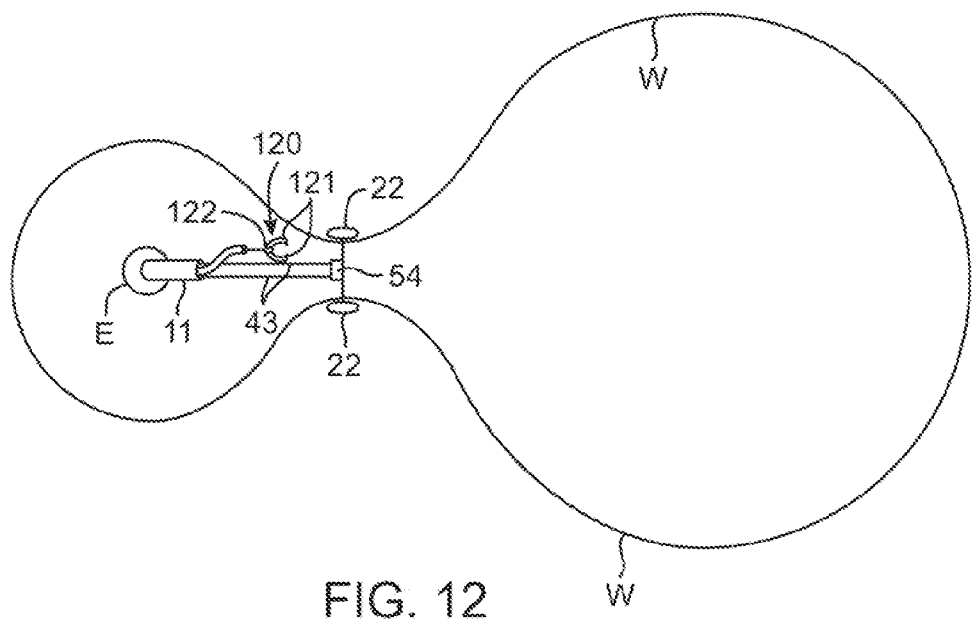
FIG. 12 is a cross-sectional view depicting the use of a pliers assembly to crimp a fastener of the present invention.
Figure 13:
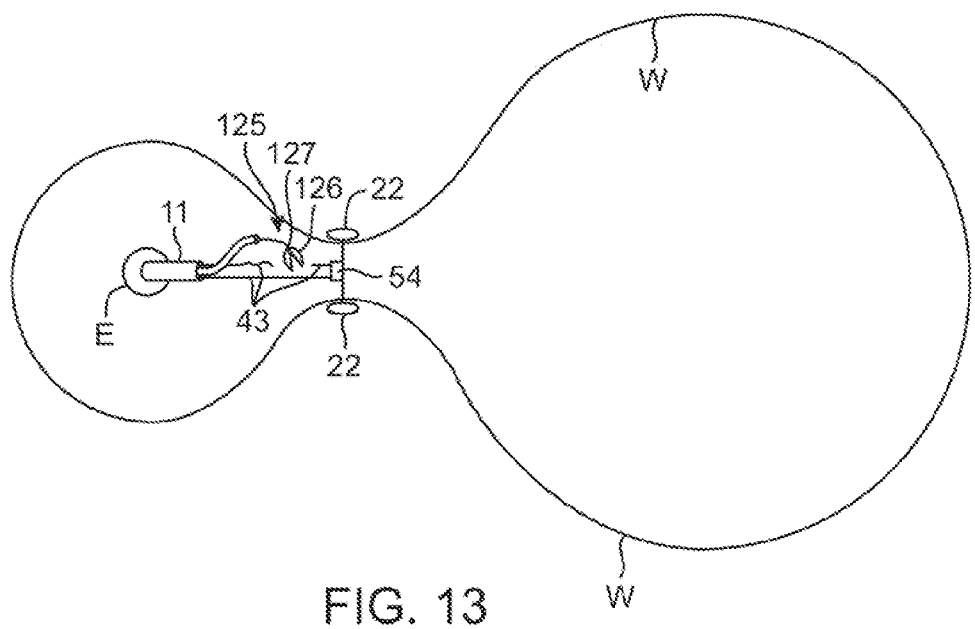
FIG. 13 is a cross-sectional view depicting the use of a scissors assembly to cut sutures of the present invention.

With respect to FIGS. 12-14, various end effectors suitable for use with the delivery catheter of FIG. 1 are described. Referring again to FIGS. 7A-7E, after sutures 43 have been threaded through fastener 54 and push rod 58 has been used to approximate the tissue walls, fastener 54 is crimped to hold the approximated tissue walls in place. Sutures 43 then are cut.

FIG. 12 illustrates pliers assembly 120, comprising arms 121 arranged to articulate about pivot point 122, which may be used to crimp fastener 54 and thereby retain sutures 43. Pliers assembly 120 is used to grip and crimp fastener 54 by manipulating an actuator disposed generally at the proximal end of catheter 11. After pliers assembly 120 is used to crimp fastener 54, it is retracted and scissor assembly 125 is advanced through catheter 11.

FIG. 13 depicts the use of scissors assembly 125, comprising blades 126 arranged to articulate about pivot point 127, to cut unneeded lengths of sutures 43 after fastener 54 has been crimped. Scissor assembly 125 is manipulated into cutting position and used to cut the sutures using an actuator disposed generally at the proximal end of catheter 11. Once sutures 43 have been cut, scissor assembly 125 is retracted through delivery catheter 11.

Figure 14A:
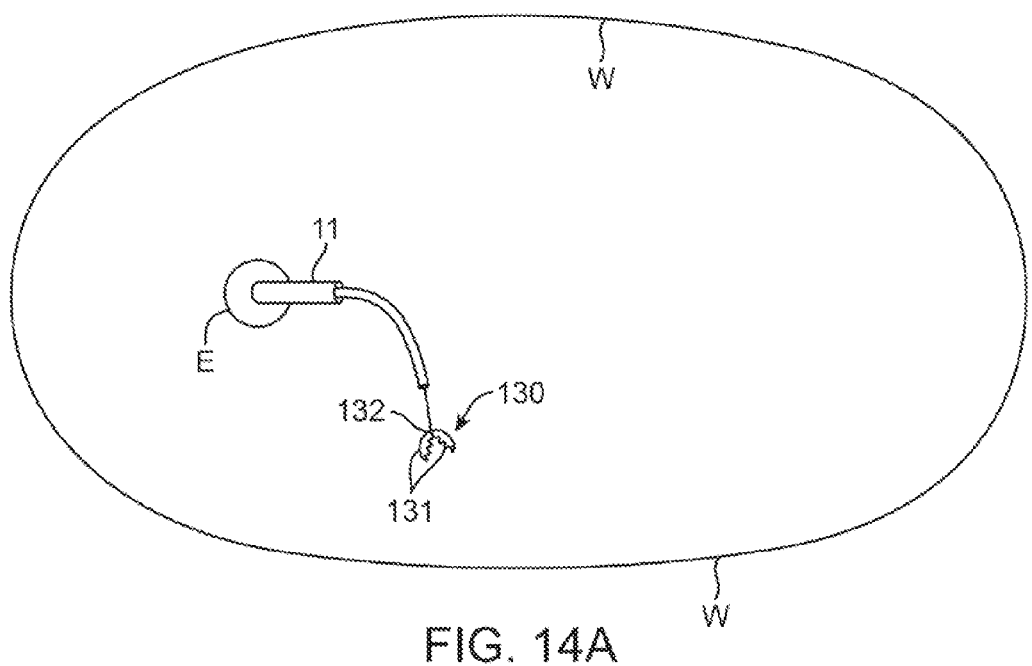
FIGS. 14A and 14B are cross-sectional views depicting the use of a jaw assembly to create a tissue fold in accordance with the principles of the present invention.
Figure 14B:
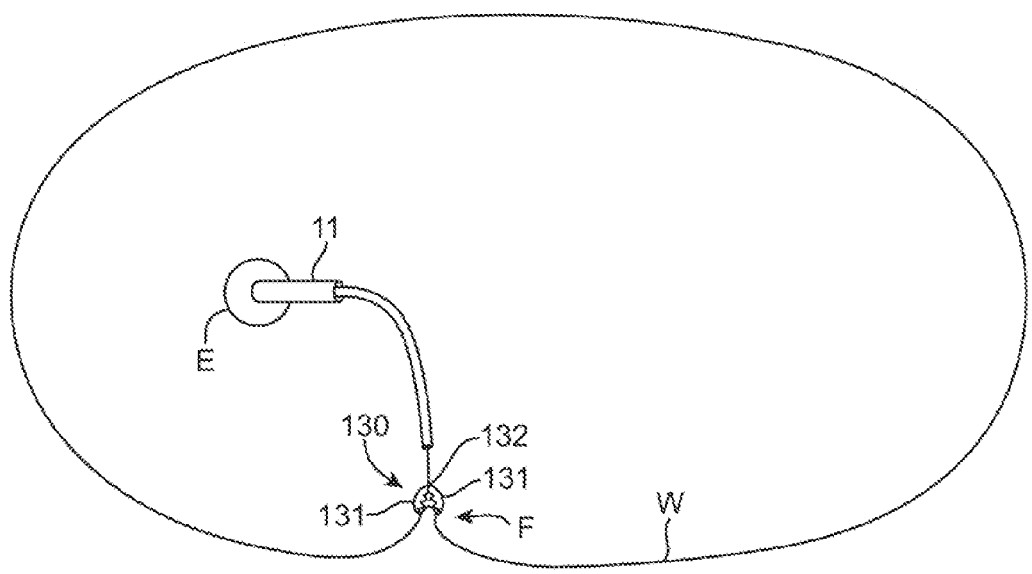

Referring now to FIGS. 14A and 14B, jaw assembly 130 is described for use in creating a tissue fold or to grab and hold tissue wall W during anchor delivery. Jaw assembly 130 comprises pair of jaws 131 arranged to rotate about pivot point 132. FIG. 14A illustrates that jaw assembly 130 may be articulated into position adjacent a tissue wall using an actuator disposed generally at the proximal end of delivery catheter 11. In FIG. 14B, jaw assembly 130 is depicted grabbing tissue wall W to create fold F in the tissue wall. Advantageously, creation of fold F facilitates the penetration of tissue wall by needle 16 and subsequent delivery of anchor assembly 22 to the opposing side of the tissue wall.

Referring to FIG. 15A, delivery catheter 11 of FIG. 1 may be configured so that needle 16 exits a lumen offset from coil screw 24. In operation, coil screw 24 is threaded into the tissue wall and retains the delivery catheter in engagement with the tissue wall while needle 16 is pushed through the tissue wall. Delivery catheter 11 may further comprise additional lumen 135 dimensioned for the passage of an endoscope, per se known in the art. Alternatively, coil screw 24 may be translatably disposed within lumen 135 (FIG. 15B), rather than mounted to a distal end of the delivery catheter.

With respect to FIGS. 16 and 17 additional alternative embodiments of stabilization devices 138 suitable for use with the delivery catheter of the present invention are described. Stabilization device 138 of FIG. 16 comprises shaft 140 disposed within lumen 135 and includes resilient fingers 142 attached thereto. When shaft 140 is moved distally, fingers 142 exit lumen 135 and self-expand to a deployed configuration. Fingers 142 then may be manipulated to create a tissue fold by grasping and pulling a tissue wall using an actuator disposed generally at the proximal end of the delivery catheter.

Stabilization device 138 of FIGS. 17A and 17B comprises a plurality of resilient curved wires 144 disposed within lumens 145 and spaced apart around the periphery of lumen 135. Curved wires 144 are connected to an actuator located generally at the proximal end of the delivery catheter. Actuation of the actuator causes curved wires 144 to be either extended from or retracted into lumens 145.

Illustratively, curved wires 144 of FIG. 17 extend radially outward when extended from lumens 145. Alternatively, curved wires 144 could extend radially inward at an oblique angle, so as to assume a partial corkscrew shape. During use, stabilization device 138 (including curved wires 144) is brought into contact with a tissue wall. Then, the wires are extended until they pierce and stabilize the tissue wall for anchor delivery.

Figure 18A:
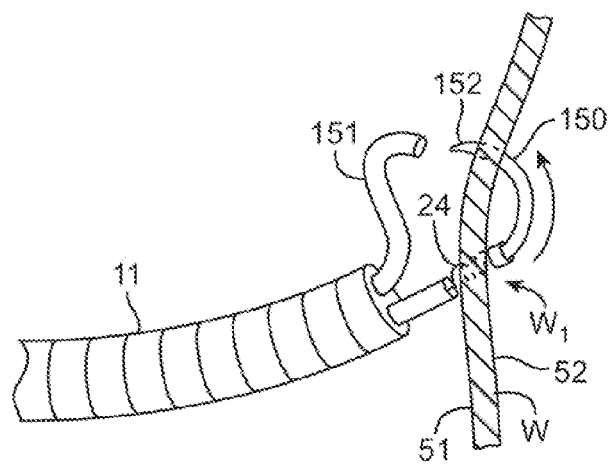
FIGS. 18A-18C are perspective views of an alternative delivery catheter featuring a curved needle according to the present invention.
Figure 18B:
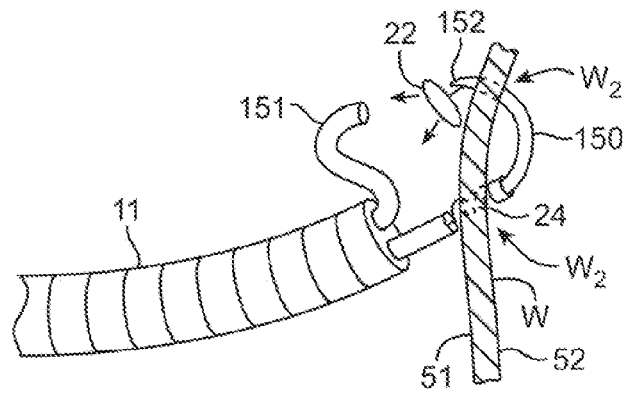
Figure 18C:
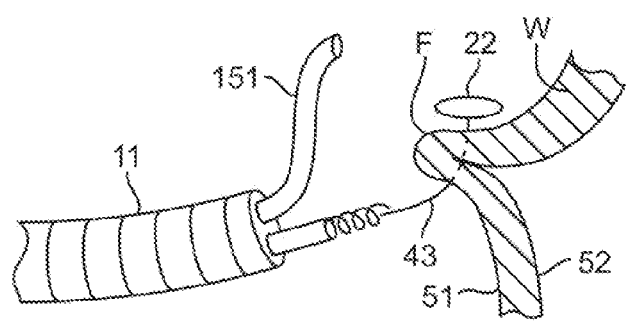

(start here) With respect to FIGS. 18A-18C, another alternative embodiment of a delivery catheter constructed in accordance with the principles of the present invention is described. Delivery catheter 11 of FIG. 18 comprises coil screw 24 and curved needle 150. In addition, endoscope 151 may be provided to visualize the site and aid in anchor delivery. Referring to FIG. 18A, once coil screw 24 has been screwed into tissue wall W, curved needle 150 is deployed through coil screw 24 such that needle 150 penetrates tissue wall W at first location W1. As the needle 150 is deployed from the distal tip of catheter 11, it curves outwardly such that full deployment results in the needle curving around and penetrating tissue wall W at second location W2. In other words, initial deployment of curved needle 150 through the coil screw causes the needle to penetrate the tissue wall (at W1) such that distal tip 152 of the needle moves from first side S1 of the tissue wall to second side S1 of the tissue wall.

Further deployment of needle 150 through the coil screw causes the needle to penetrate the tissue wall for a second time (at W2) such that distal tip 152 moves from the second side of the tissue wall back to the first side of the tissue wall. Referring to FIG. 18B, anchor assembly 22 is ejected through the needle after distal tip 152 penetrates the tissue wall for the second time. After ejecting anchor assembly 22, the needle is retracted. Referring to FIG. 18C, tensioning of the suture 43 produces fold F in tissue wall W between first location W1 and second location W2.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A delivery catheter for a gastric reduction system, the delivery catheter comprising:
    an elongate torqueable and flexible tube having a back end and a front end;
    a needle translatably disposed within the tube, with the needle having a penetrating tip;
    at least one anchor translatably disposed within the needle, and moveable out of the penetrating tip of the needle; and
    a coil on a front end of a shall that is translatably disposed within a lumen in said tube, said coil being extendible out of the front end of the tube.

2. The delivery catheter of claim 1, wherein the tube is formed of a braided wire.

3. The delivery catheter of claim 1, wherein the tube contains a plurality of slots disposed substantially perpendicular to a longitudinal axis of the tube.

4. The delivery catheter of claim 3, wherein the slots are formed in a sinusoidal pattern.

5. The delivery catheter of claim 3, wherein the slot density is increased near a distal end of the tube.

6. The delivery catheter of claim 1, wherein the coil includes a sharpened distal tip to facilitate tissue penetration.

7. The delivery catheter of claim 1, wherein the coil comprises a plurality of coils that form a central opening for the passage of the needle.

8. The delivery catheter of claim 1, wherein the coil and needle are substantially coaxial.

9. The delivery catheter of claim 1, further comprising a push rod translatably disposed within the needle and adapted to push the anchor out of a distal end of the needle.

10. A catheter comprising:
    a flexible tube having a front end and a back end;
    a needle within the tube and having a tip extendible out of the front end of the tube;
    at least one anchor positioned within the flexible tube and moveable out of the flexible tube during a surgical procedure;
    a suture connected to one or more of the anchors, and with the suture extending within the tube towards the back end of the tube; and
    a coil on a front end of a shall that is translatably disposed within a lumen in said tube, said coil being extendible out of the front end of the tube.

11. The catheter of claim 10 wherein the tube is torqueable and is formed of braided wire.

12. The catheter of claim 10 wherein the tube contains a plurality of slots extending substantially perpendicular to a longitudinal axis of the tube, to increase the flexibility of the tube.

13. The catheter of claim 10, wherein said coil has a sharp tip.

14. The catheter of claim 13 with the needle having a penetrating tip adjacent to the front end of the flexible tube.

15. The catheter of claim 13 with the needle positioned to extend out of the front end of the flexible tube and through the coil.

16. The catheter of claim 10 further comprising a push rod longitudinally moveable within the needle for pushing one or more anchors out of the tip of the needle.

17. The catheter of claim 10 with the needle having non-coring tip.

18. The catheter of claim 10 with the tube having a coating of fluorine resins.

19. A catheter comprising:
    a flexible and torqueable tube having a front end and a back end;
    a needle within the tube and having a piercing tip extendible out of the front end of the tube;
    one or more anchors stored within the tube and moveable out of the tube for placement during a surgical procedure;
    a suture connected to the anchor and leading out towards the back end of the tube; and
    a coil on a front end of a shaft that is translatably disposed within a lumen in said tube, said coil being extendible out of the front end of the tube.

20. The catheter of claim 19 wherein the tube having through slots to increase the flexibility of the tube.

21. The catheter of claim 19 further comprising a push rod longitudinally moveable within the needle for pushing an anchor out of the tip of the needle.

22. A catheter comprising:
    a flexible and torqueable tube having a front end and a back end;
    a handle attached adjacent to the back end of the tube;
    a hollow needle within the tube and having a piercing tip extendible out of the front end of the tube;
    one or more anchors within the needle, with the anchor moveable out of the piercing tip of the needle;
    an anchor ejector within the needle;
    a suture connected to the anchor and leading out towards the handle;
    a needle control on the handle linked to the needle, for moving the needle within the tube;
    an anchor ejector control on the handle linked to the anchor ejector; and
    a coil on a front end of a shaft that is translatably disposed within a lumen in said tube, said coil being extendible out of the front end of the tube.

23. A catheter comprising:
    a flexible tube having a front end and a back end;
    a needle within the tube and having a tip extendible out of the front end of the tube;

at least one anchor positioned within the needle and moveable out of the needle tip during a surgical procedure;

a suture connected to one or more of the anchors, and with the suture extending within the tube towards the back end of the tube; and a coil on a front end of a shaft that is translatably disposed within a lumen in said tube, said coil being extendible out of the front end of the tube.

* * * * *